(12) United States Patent
Ikuta

(10) Patent No.: US 10,314,469 B1
(45) Date of Patent: Jun. 11, 2019

(54) SPECTRALLY ENCODED PROBES

(71) Applicant: CANON U.S.A., INC., Melville, NY (US)

(72) Inventor: Mitsuhiro Ikuta, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 15/969,298

(22) Filed: May 2, 2018

(51) Int. Cl.
  *G01J 3/00* (2006.01)
  *A61B 1/06* (2006.01)
  *A61B 1/00* (2006.01)
  *A61B 1/07* (2006.01)

(52) U.S. Cl.
  CPC ........ *A61B 1/0646* (2013.01); *A61B 1/00006* (2013.01); *A61B 1/00009* (2013.01); *A61B 1/00096* (2013.01); *A61B 1/00117* (2013.01); *A61B 1/063* (2013.01); *A61B 1/0669* (2013.01); *A61B 1/07* (2013.01)

(58) Field of Classification Search
  CPC ...... G01J 3/02; G01J 3/28; G01J 3/42; G01N 21/31; G01N 21/552
  USPC .......................................................... 356/300
  See application file for complete search history.

(56) References Cited

U.S. PATENT DOCUMENTS

| | | | |
|---|---|---|---|
| 6,341,036 B1 | 1/2002 | Tearney et al. | |
| 7,769,270 B2 | 8/2010 | Nakamura et al. | |
| 7,843,572 B2 | 11/2010 | Tearney et al. | |
| 7,859,679 B2 | 12/2010 | Bouma et al. | |
| 8,045,177 B2 | 10/2011 | Tearney et al. | |
| 8,145,018 B2 | 3/2012 | Shishkov et al. | |
| 8,780,176 B2 | 7/2014 | Yelin | |
| 8,812,087 B2 | 8/2014 | Yelin | |
| 9,791,317 B2 | 10/2017 | Shishkov et al. | |
| 2008/0013960 A1 | 1/2008 | Tearney et al. | |
| 2008/0262297 A1 | 10/2008 | Gilboa et al. | |
| 2009/0052305 A1* | 2/2009 | Koreeda | G11B 7/1353 369/112.23 |
| 2011/0237892 A1 | 9/2011 | Tearney et al. | |

(Continued)

FOREIGN PATENT DOCUMENTS

WO 2015/116939 A1 8/2015
WO 2015/116951 A1 8/2015

OTHER PUBLICATIONS

Yelin, D., et al., "Three-dimensional miniature endoscopy", Nature, Oct. 19, 2006, p. 765, vol. 443.

(Continued)

*Primary Examiner* — M D M Rahman
(74) *Attorney, Agent, or Firm* — Canon USA Inc., IP Division

(57) ABSTRACT

A forward-viewing spectrally encoded endoscope (SEE) probe includes a light guiding component, a light focusing component, and a grating component arranged along a longitudinal axis of a drive cable. The SEE probe is configured for guiding light from the light guiding component, through the light focusing component, and to the grating component, and then forwarding a spectrally dispersed light line from the grating component towards an image plane. One or more of the light guiding component, the light focusing component, and the grating component is arranged at an angle with respect to the longitudinal axis of the drive cable so that at least one wavelength of the spectrally dispersed light line goes to the direction of axis of the drive cable.

11 Claims, 11 Drawing Sheets

(56) References Cited

U.S. PATENT DOCUMENTS

2012/0076160 A1\* 3/2012 Caffey .................. B82Y 20/00
372/20
2016/0341951 A1 11/2016 Tearney et al.
2017/0322079 A1 11/2017 Do et al.
2018/0017778 A1 1/2018 Ikuta et al.

OTHER PUBLICATIONS

Tearney, G. J., "Spectrally encoded miniature endoscopy", Optics Letters, Mar. 15, 2002, pp. 412-441, vol. 27, No. 3.
Pitris, C. et al., ("A GRISM-based probe for spectrally encoded confocal microscopy" Optics Express, Jan. 27, 2003, pp. 120-124, vol. 11, No. 2.
Kang, D., et al., "Spectrally-encoded color imaging", Optics Express, Aug. 17, 2009, pp. 15239-15247, vol. 17, No. 17.

\* cited by examiner

FIG. 3
STEP 1
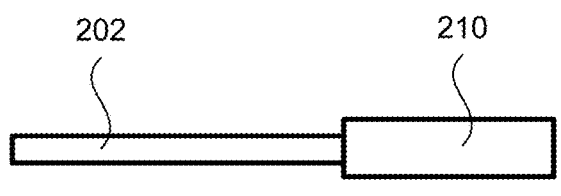
STEP 2
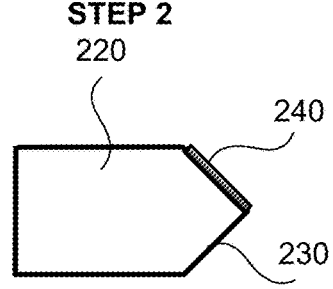
STEP 3
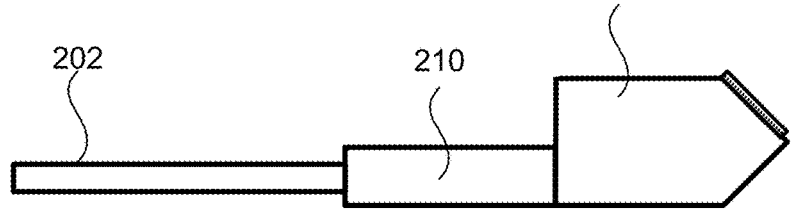
STEP 4
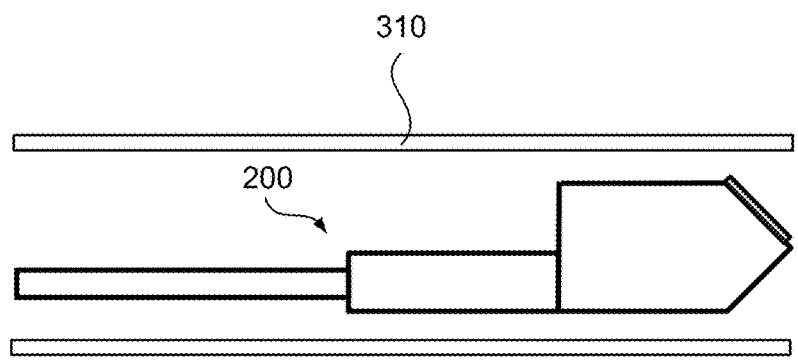

SPECTRALLY ENCODED PROBES

CROSS-REFERENCE TO RELATED APPLICATIONS n/a

FIELD OF THE DISCLOSURE

The present disclosure generally relates to endoscopes, and in particular the present disclosure relates to a method of aligning distal optics of spectrally encoded endoscopic probes.

BACKGROUND INFORMATION

Medical endoscopic probes have the ability to provide images from inside a patient's body. Considering the potential damage to a human or animal body caused by the insertion of a foreign object, it is preferable for the endoscopic probe to be as small as possible. Additionally, for non-medical applications, the ability to image within small conduits such as small ducts, pipes, tubing, and internal inspection through cracks and other tight spaces, etc., requires a probe of small size.

One useful medical probe employs spectrally encoded endoscopy ("SEE"), which is a miniature endoscopy technology that can conduct high-definition imaging through a sub-mm diameter probe. In a typical SEE probe, broadband light is diffracted by a grating at the distal end of an optical fiber to produce a dispersed spectrum of different wavelengths (colors) on a sample. Light returned from the sample is detected using a spectrometer; and each resolvable wavelength corresponds to reflectance from a different point on the sample. Thus, a SEE probe encodes light reflected from a given point in the sample by wavelength. The principle of the SEE technique and a SEE probe with a diameter of 0.5 mm (500 μm) have been described by D. Yelin et al., in a publication entitled "Three-dimensional miniature endoscopy", Nature Vol. 443, 765-765 (2006). Another similar example is described by G. Tearney et al., in "Spectrally encoded miniature endoscopy", Opt. Lett., 27(6): p. 412-414, 2002. Imaging with SEE can produce high-quality images in two- and three-dimensions.

Spectrally-encoded endoscopy utilizes the ability of the diffraction grating that deflects incident light to a diffraction angle according to wavelength. When the deflected light hits an object, light is scattered by the object. Detecting the scattered light intensity at each wavelength is equivalent to detecting the intensity from the corresponding diffraction angle. Thus, a one-dimensional, line image of the object can be obtained. A two-dimensional image is obtained by rotating the SEE probe. A three-dimensional image can be obtained by rotating and translating (moving linearly) the SEE probe. Moreover, when incorporated into a sample arm of an interferometer, the SEE probe can also acquire depth information from a sample (e.g., tissue).

Spectrally-encoded endoscopy probes are designed with side-viewing or forward-viewing characteristics. Forward view SEE probes are preferable for many applications. Forward view SEE imaging is particularly advantageous for applications such as orthopedics, ear, nose and throat (ENT), laparoscopy, and pediatric surgery. The forward-viewing (or front-view) probe type consists of multiple components including lenses, spacer elements, prisms and gratings, which makes the probe design complicated. Examples of such designs can be found, for example, in C. Pitris et al., Optical Express Vol. 11 120-124 (2003) and U.S. Pat. No. 8,145,018, both of which disclose a dual prism configuration where a grating is sandwiched between two prisms (a "grism"). The grism directs spectrally dispersed light such that at least one of the wavelengths propagates parallel to the optical axis of the probe. The grism consists of multiple components (grating, prisms) which need proper alignment. The need of a grism to construct a forward-view probe increases the cost, complexity of fabrication and size of the probe. Publication WO2015/116951 discloses another forward view endoscope where an angled reflective side surface makes the light incidence angle on the grating such that at least one of the wavelengths propagates parallel to the optical axis of the lens. However, these known designs of forward view SEE probes have drawbacks.

In particular, due to miniature size of the optics, the alignment of the spacer and the lens poses challenges during fabrication. Further, the illumination fiber is generally arranged off-axis to the GRIN lens, which introduces additional difficulties in fabrication as well as optical aberrations.

Accordingly, it can be beneficial to address and/or overcome at least some of the deficiencies indicated herein above, and thus to provide a new SEE probe having forward direction view, and an apparatus to use such a probe, e.g., for imaging in a small optics.

SUMMARY

According to at least one embodiment of the present disclosure, there is provided a method of aligning the distal optics of an endoscopic probe comprising: aligning a light guiding component; a light focusing component; and a light diffusing component (e.g., a grating), such that light which is put into the proximal end of light guiding component can emit from the distal end thereof focused by the focusing component onto the light diffusing component to thereby generate a dispersed light line, and arranging the light guiding component, light focusing component and light diffusing component within a drive cable so that at least one wavelength of the dispersed light line goes to the direction of axis of the drive cable.

According to another embodiment, a probe having a proximal end and a distal end arranged inside a drive cable, comprises: a light guiding component; a light focusing component; and a grating component. The probe is configured for guiding light from the light guiding component, through the light focusing component, and to the grating component, and then forwarding a spectrally dispersed light line from the grating component towards a sample, wherein an optical component assembly of the probe is arranged in the drive cable so that at least one wavelength of the spectrally dispersed light line goes to the direction of axis of the drive cable.

According to yet another embodiment, there is disclosed a system comprising: light source, a probe having a proximal end and a distal end arranged inside a drive cable, a rotary element connected to the distal end of the probe, one or more detection fibers surrounding the proximal end of the probe, one or more detectors, and one or more processors. The probe is configured for guiding light from the light source through the light guiding component, through the light focusing component, and to the grating component, and then forwarding a spectrally dispersed light line from the grating component towards a sample, wherein an optical component assembly of the probe is arranged in the drive cable so that at least one wavelength of the spectrally dispersed light line goes to the direction of axis of the drive cable.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 3 illustrates an example of a fabrication process for assembling the SEE probe.

DETAILED DESCRIPTION OF EMBODIMENTS

Figure 1:
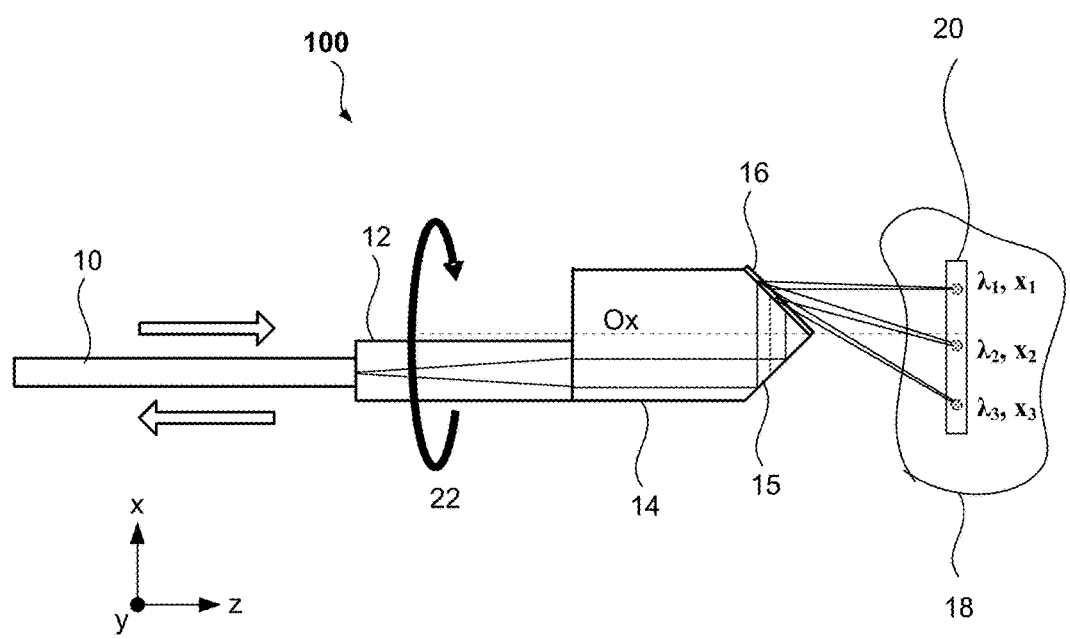
FIG. 1 is a diagram of an exemplary SEE probe according to an exemplary embodiment of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

The embodiments disclosed herein describe SEE probes that can have good resolution in both the scanning direction and the spectral direction due to a fuller use of the available field of view. These embodiments also provide images with minimal distortion.

<SEE Probe Structure>

FIG. 1 shows a diagram of an exemplary embodiment of a forward view SEE probe 100 according to the present disclosure. The exemplary SEE probe 100 includes, from its proximal end to distal end thereof, an optical fiber 10 (light guiding component), a focusing or collimating lens 12 (light focusing component), and a spacer assembly 14 arranged along an axis Ox. The spacer assembly 14 includes a mirror surface 15 and a diffraction grating 16 (grating component). Broadband light or other electro-magnetic radiation (shown as left-to-right arrow) can be coupled or otherwise provided to the fiber 10 from a non-illustrated light source. The light or electro-magnetic radiation is focused by the lens 12 to form a substantially collimated light beam. The light (or other electro-magnetic radiation) travels through the focusing lens 12, the spacer 14, is reflected by the mirror surface 15, and then incident on the grating 16. At the grating 16, the light is diffracted according to its wavelength and incidence angle. Each diffracted light (having a wavelength λ or a wavelength band Δλ) is focused on a unique spatial location on a target sample 18 (e.g., tissue).

As shown in FIG. 1, positions $X_1$, $X_2$, and $X_3$ are unique spatial locations on the sample 18 where dispersed light of wavelengths $\lambda_1$, $\lambda_2$, and $\lambda_3$, respectively, imping on the sample to form a spectrally dispersed light line 20. In other words, grating 16 causes the light (or other electro-magnetic radiation) to be focused into a plane or line 20 formed on the sample. The plane or line 20 shown in FIG. 1 is referred to as a spectrally-encoded line. The grating 16 is designed to cause one of the wavelengths (e.g., λ1 in FIG. 1) in the light beam to propagate substantially parallel to the axis (Ox) of the probe 100. The other wavelengths (e.g., $\lambda_2,\lambda_3$, etc.) are diffracted at different angles with respect to the axis Ox. Light (or other electro-magnetic radiation) scattered by the sample 18 can be coupled or otherwise provided back to the fiber 10 or to a different fiber (not shown), and then the collected light can be delivered to a detector (not shown) that includes a spectrometer (not shown). At the spectrometer, the spectrum of the returning light (or other electro-magnetic radiation) can be read out as an electrical signal, which can then be used to generate a line image of the tissue using a computer or other digital processor (not shown).

In order to acquire two-dimensional (2D) images of the target sample (e.g., cavities such as vessels, esophagus and nasal cavity, generally referred to as "bodily lumens"), the exemplary SEE probe 100 can be scanned rotationally around the axis Ox as shown by the rotational arrow 22, e.g., by rotating or oscillating the probe in ways which should be understood to those having ordinary skill in the art. In addition, the probe 100 can be moved (translated) longitudinally so that images of a target sample are obtained at different depths or different working distances. This longitudinal movement may be performed by pulling the tip (distal end) of the probe back towards the proximal end in a process referred to as a "pullback" operation.

Figure 2A:
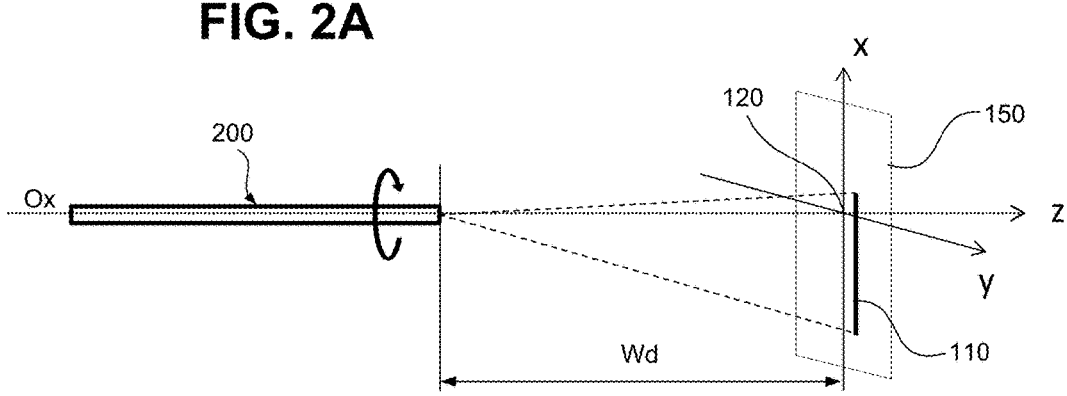
FIG. 2A shows imaging parameters of an exemplary SEE probe having forward view characteristics.

FIG. 2A shows imaging parameters of an exemplary SEE probe 200. In FIG. 2A, the diffracted light emitted from the exemplary SEE probe 200 is incident on an imaging plane 150 (illumination plane) to form a spectrally dispersed (encoded) illumination line no at a working distance (Wd). As shown in FIG. 2A, the probe axis Ox is the z axis; at the imaging plane 150, the probe axis passes through a center point 120 where the z axis crosses the x and y axes. When any of the optics of SEE probe 200 is misaligned, for example when the grating groove direction is tilted on the probe, or the bonding of the illumination fiber to the lens is defective, the illumination line no is shifted from the center 120 of the imaging plane iso. As a result, at least portion of the light line no does not go in the direction of the probe axis.

Figure 2B:
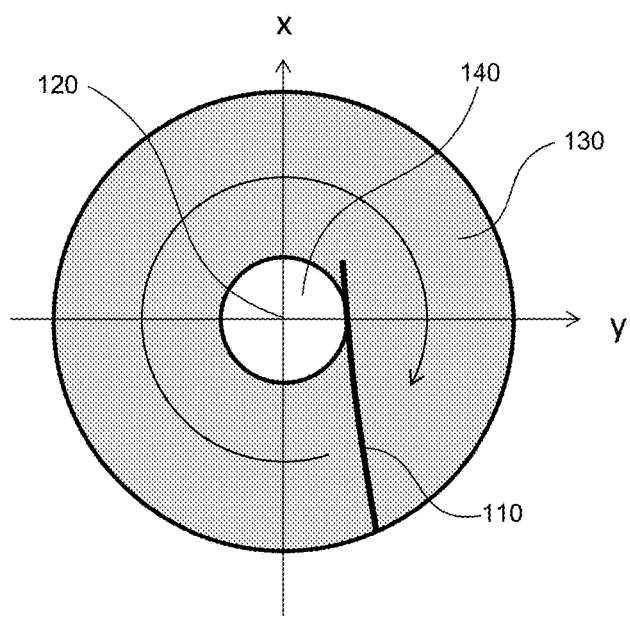
FIG. 2B shows a spectrally encoded illumination line 110 as seen at the field of view (FOV) of a SEE probe.

FIG. 2B shows the spectrally encoded illumination line no as seen at the field of view (FOV) of SEE probe 200, when the SEE probe is rotated. By rotating the probe 200 around the axis Ox, the spectrally encoded line no can scan the target sample in a two-dimensional (2D) area 130. However, when the illumination line 110 is shifted from the center 120, there will be an area 140 at center of field of view where no illumination light hits. This means that no information can obtained from this area 140 of the target sample in the SEE image reconstruction process. In other words, the non-illuminated area 140 acts as an obscuration area in the center of the field of view. To avoid this obscuration and to be able to obtain information from the area 140, the distal end of the probe could be moved or tilted in the x and y directions of the imaging plane iso, but such movement may be mechanically restricted or could be detrimental to the subject. In addition, when imaging small-sized tubular target samples (e.g., when imaging narrow lumens such as capillaries), it may not possible to move or tilt the probe in the x and y directions of the imaging plane due to spatial limitations. Therefore, in accordance with at least one embodiment of the present disclosure, appropriate alignment of the distal optics of the probe 200 ensures that no obscuration occurs in the center of the field of view. Expressed in another way, appropriate alignment of the distal optics of the probe 200 ensures that the entire field of view is appropriately illuminated so that better imaging can be achieved.

<Probe Fabrication Process>

FIG. 3 illustrates an example of a fabrication process for assembling the SEE probe 200. At STEP 1, of FIG. 3, a fiber 202 and a lens 210 are assembled together by bonding or splicing in a manner known to those skilled in the art. In parallel, at STEP 2, an spacer assembly 220 is constructed by polishing a glass rod into the desired spacer shape, and then making a mirror surface 230, and forming a grating 240. It should be understood that the drawing provided in FIG. 3 shows exemplary fiber, lens, and spacer elements for illustration only. The shape and dimensions of these elements are not limiting, as these elements make take numerous other shapes or dimensions. For example, for the spacer, several glass (or plastic) rods with different diameters can be used. To form the mirror surface 230 and the grating 240, the glass rod can be polished at the desired angle. After polishing, the polished surface can be cleaned and polished to form the mirror, and in the same manner the grating 240 may be formed on a different polished surface of spacer 220.

At STEP 3, the lens 210 is assembled together with the spacer assembly 220, e.g., by bonding or splicing. As a result, the distal optics of the probe 200 are assembled. Now, at STEP 4, the distal optics and fiber of the probe 200 are inserted into a drive cable 310 (drive cable or guide cable), and fixed therein to form an integral body. Finally, the drive cable 310 containing the distal optics of probe 200 therein-side is further arranged inside an inner sheath 320 of an endoscope assembly, as further described below. As it will be appreciated by those skilled in the art appropriate alignment of the distal optics in probe 200 is important for high-quality imaging. However, even if care is taken to align the fiber with the distal optics, it is unlikely that perfect alignment can be achieved and more likely that there will be some lateral and rotational misalignment between the fiber and the distal optical elements.

Figure 4:
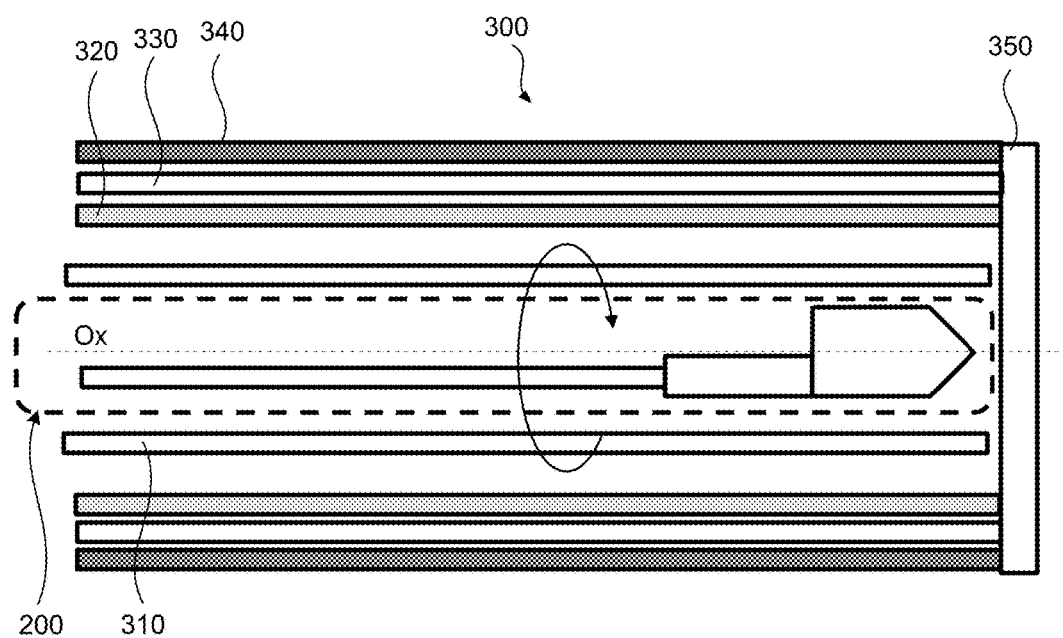
FIG. 4 shows an exemplary assembled SEE endoscope.

FIG. 4 shows an assembled SEE endoscope 300 containing thereinside the SEE probe 200. In the endoscope 300, the distal optics of the assembled probe 200 are arranged inside the inner diameter of the drive cable 310, for example, by bonding. The distal optics of probe 200 along with the drive cable 310 is rotated inside the inner sheath 320 by a non-illustrated torque generating motor located at the proximal end of the probe. At least at the distal end of the endoscope assembly, detection fibers 330 are arranged around the outer surface of the inner sheath 320. To protect the detection fibers, an outer sheath 340 covers the detection fibers 330. At the distal tip of the outer sheath 340, a transparent window cover 350 is provided so as to cover at least the distal optics of the probe 200 and the detection fibers 330.

During the assembly process of steps 1-4 in FIG. 3, fabrication errors can occur due to an accumulation of misalignments of the distal optics, or misalignment of the SEE probe 200 inside drive cable 310. Specifically, as it will be appreciated by those skilled in the art appropriate alignment of the distal optics in probe 200 is important for high-quality imaging. However, even if care is taken to align the imaging fiber with the distal optics, it is unlikely that perfect alignment can be achieved and more likely that there will be some lateral and rotational misalignment between the fiber and the distal optical elements. This accumulation of small misalignments causes the spectrally encoded illumination line no to not pass trough the center of the field of view. Such fabrication error includes misalignment of the fiber 202 and lens 210, misalignment of the mirror surface 230 (e.g., due to errors in polishing), misalignment of the surface of grating 240 (e.g., due to errors in the fabrication of the spacer), misalignment in direction of the grating pattern, and misalignment of bonding the lens 210 and spacer 220. For example, as described in more detail below, if the grating pattern is tilted by 1 degree, the spectrally encoded illumination line from the illumination optics of the design described above can be shifted from the optical axis by about 1.6 degrees in terms of the viewing angle, when n=1.528, and the mirror and grating surface angles, $\Theta_M$ and $\Theta_G$ are 41.4 and 42.7 degrees, respectively. The grating 240 has 650 lines/mm groove density. In this case, 416 nm light is diffracted in $-6^{th}$ order in direction of the axis Ox of the probe 200 for blue color. In this example, the ratio 1:1.6 between pattern tilt and illumination line shift angles is calculated from equation (13), which is discussed in more detail below, for specific probe parameters. In other words, the ratio between pattern tilt and illumination line shift angles is different at different probe parameters.

<SEE Probe Geometrical Parameters>

Figure 5:
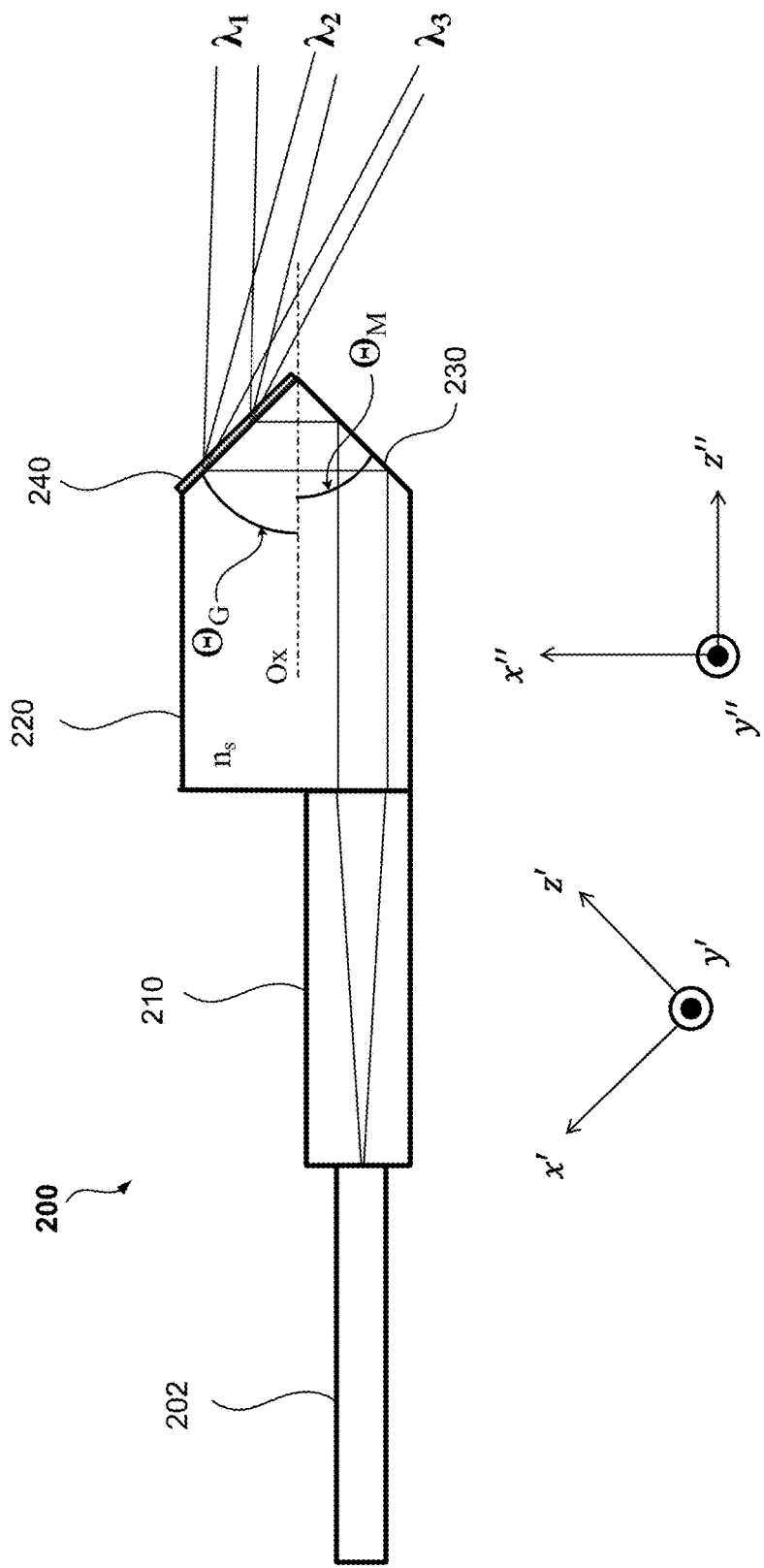
FIG. 5A shows geometrical parameters in an example of distal optics of the SEE probe, according to an embodiment.
FIG. 5B shows a Cartesian coordinate system (first coordinate system) x", y", z".
FIG. 5C shows a Cartesian coordinate system (second coordinate system) x', y', z'.

FIG. 5A shows the geometrical parameters in an example of the distal optics of the SEE probe 200, according to an embodiment. As shown in FIG. 5A, the distal optics includes the fiber 202 bonded to the lens 210, and the lens 210 in turn connected to the spacer 220. The spacer 220 includes the mirror surface 230 and the grating 240. In an embodiment, the fiber 202 can be a single mode fiber or multimode fiber. The lens 210 can be a graded-index (GRIN) lens or a ball lens. The spacer 220 can be made of glass or molded plastic.

Through the fiber 202 broadband light is delivered from a non-illustrated light source, and the light guided to the GRIN lens 210. The light is then collimated by the lens 210 and a collimated beam is delivered on to the spacer 220. The spacer 220 can have a light reflecting surface, such as mirror surface 230. The mirror surface 230 can be made by polishing a part of the spacer or coating a part of the spacer with a reflective metal layer. The light beam traveling through the spacer 220 is incident on the mirror surface 230 at an angle larger than the critical angle with respect the mirror surface 230, and therefore the light incident on the surface 230 is completely reflected towards the grating 240. The grating 240 has a grating pattern formed on another surface of the spacer 220. The grating pattern can be made of glass or resin in a known manner. The light reflected at the mirror surface 230 is incident on the grating surface of the grating 24o and then diffracted towards a target sample (not shown). The diffracted light goes to the target sample as illumination light in spectrally encoded light having different wavelengths ($\lambda_1$, $\lambda_2$, $\lambda_3$) incident on different points of the target sample.

The fiber can be a singlemode fiber or multimode fiber. The lens can be a GRIN lens or a ball lens. The spacer can be made of glass or plastic. Thought the fiber broadband light (or monochromatic light) is delivered from a light source to the lens. In one exemplary embodiment, the spacer material has a refractive index n=1.528, and the mirror and grating surface angles, $\Theta_M$ and $\Theta_G$ are 41.4 and 42.7 degrees, respectively. The grating 240 has 650 lines/mm groove density. In this case, 416 nm light is diffracted in $-6^{th}$ order in direction of the axis Ox of the probe 200 for blue color. For green and red color, 498 nm and 621 nm respectively, light is diffracted in $-5^{th}$ and $-4^{th}$ order in.

In the forward view SEE probe 200 shown in FIG. 5A, we define a Cartesian coordinate system (first coordinate system) x", y", z" so that the probe optical axis is the z" axis, and the mirror normal and grating normal are in the x"-z" plane. FIG. 5B shows the Cartesian coordinate system (first coordinate system) x", y", z". We also define another Cartesian coordinate system (second coordinate system) x', y', z', so that the z' axis is parallel to the grating surface normal, and the y' axis is parallel to y" axis. FIG. 5C shows the Cartesian coordinate system (second coordinate system) x', y', z'.

<SEE Probe Inclination Angle Calculation and Simulation>

Figure 6:
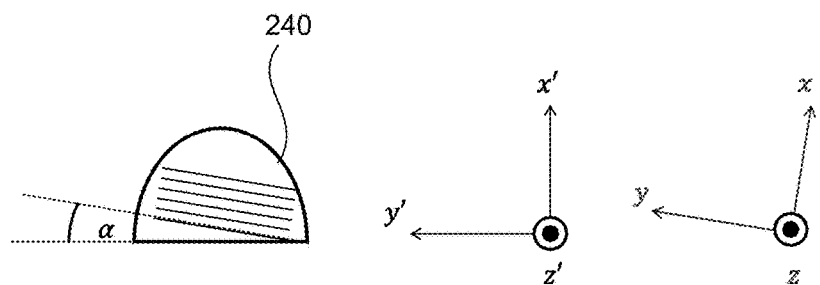
FIG. 6 shows grating surface parameters as viewed from the normal to the surface of the grating.

FIG. 6 shows the grating surface viewed from the normal to the surface of the grating 240. Here, we introduce another Cartesian coordinate system (a third coordinate system) x, y, z, so that the grating lattice vector is parallel to the x axis, and the z axis is parallel to z' axis. In this third coordinate system, it is assumed the grating pattern (x direction in FIG. 6) is tilted by an angle $\alpha$ with respect to the x' direction.

Figure 7:
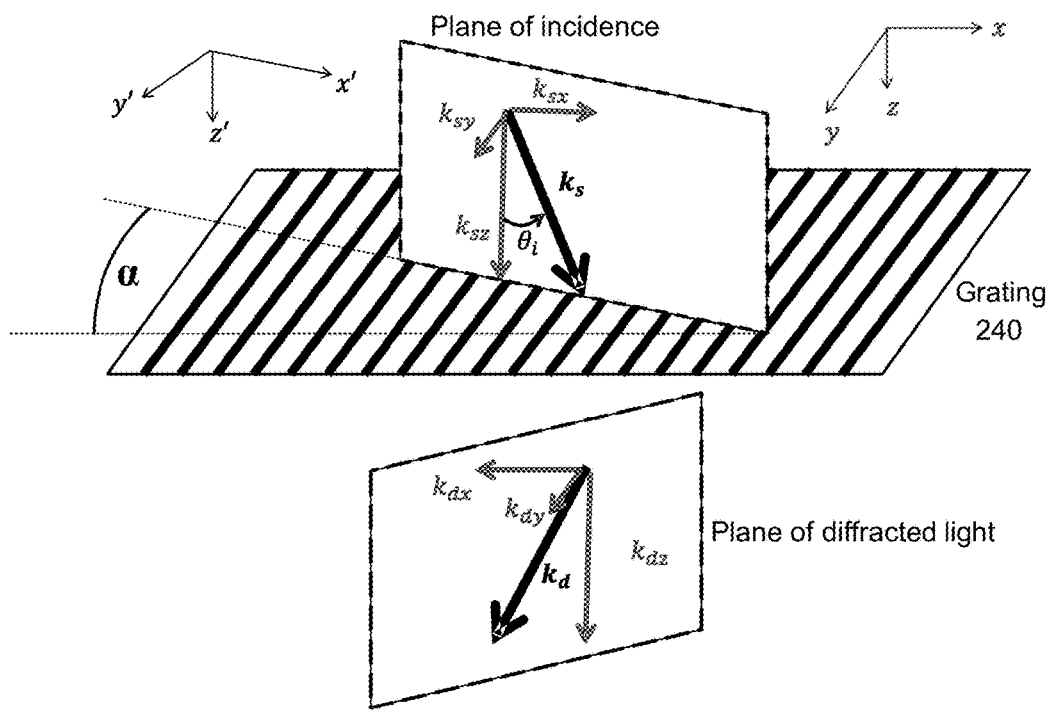
FIG. 7 shows the plane of incidence and the plane of diffracted light of the grating 240 as seen in another Cartesian coordinate system (a third coordinate system) x, y, z.

Now, considering the three different Cartesian coordinate systems defined above, FIG. 7 shows the plane of incidence and the plane of diffracted light of the grating 240. In FIG. 7, we now define a wave vector of a chief ray of an incident beam in the spacer 220 as $k_s$, and a wave vector of the diffracted beam in air as $k_d$. We then define each component of vectors $k_s$ and $k_d$ in the coordinate system x, y, z, as ($k_{sx}$, $k_{sy}$, $k_{sz}$), and ($k_{dx}$, $k_{dy}$, $k_{dz}$), respectively.

Based on the foregoing definitions, we can now calculate the magnitude of the wave vectors as follows. The magnitude of the wave vectors are $$k_s = \frac{2\pi n_s}{\lambda} \text{ and} \quad \text{Equation (1)}$$

$$k_d = \frac{2\pi}{\lambda} \quad (2)$$

where $\lambda$ is the wavelength in vacuum and $n_s$ is the refractive index of the material of spacer 220.

From the geometry defined in FIGS. 6 and 7, we obtain Equation (3)

$$\begin{pmatrix} k_{sx} \\ k_{sy} \\ k_{sz} \end{pmatrix} = k_s \begin{pmatrix} \sin\theta_i \cos\alpha \\ \sin\theta_i \sin\alpha \\ \cos\theta_i \end{pmatrix} \text{ where} \quad (3)$$

$$\theta_i = 2\Theta_M + \Theta_G - \frac{\pi}{2}. \quad (4)$$

Each component of $k_d$ is calculated by $$k_{dx} = k_{sx} + 2\pi mG \quad (5)$$

$$k_{dy} = k_{sy} \quad (6)$$

and $$k_{dz} = \sqrt{k_d^2 - k_{dx}^2 - k_{dy}^2}. \quad (7)$$

The components of $k_d$ in coordinate system x', y', z', are $$\begin{pmatrix} k_{dx'} \\ k_{dy'} \\ k_{dz'} \end{pmatrix} = \begin{pmatrix} \cos\alpha & \sin\alpha & 0 \\ -\sin\alpha & \cos\alpha & 0 \\ 0 & 0 & 1 \end{pmatrix} \begin{pmatrix} k_{dx} \\ k_{dy} \\ k_{dz} \end{pmatrix} \quad (8)$$

and the components of $k_d$ in coordinate system x", y", z" are $$\begin{pmatrix} k_{dx''} \\ k_{dy''} \\ k_{dz''} \end{pmatrix} = \begin{pmatrix} \cos(\frac{\pi}{2}-\Theta_G) & 0 & \sin(\frac{\pi}{2}-\Theta_G) \\ 0 & 1 & 0 \\ -\sin(\frac{\pi}{2}-\Theta_G) & 0 & \cos(\frac{\pi}{2}-\Theta_G) \end{pmatrix} \begin{pmatrix} k_{dx'} \\ k_{dy'} \\ k_{dz'} \end{pmatrix} \quad (9)$$

$$= \begin{pmatrix} \sin\Theta_G & 0 & \cos\Theta_G \\ 0 & 1 & 0 \\ -\cos\Theta_G & 0 & \sin\Theta_G \end{pmatrix} \begin{pmatrix} k_{dx'} \\ k_{dy'} \\ k_{dz'} \end{pmatrix}$$

$$= \begin{pmatrix} \sin\Theta_G\cos\alpha & \sin\Theta_G\sin\alpha & \cos\Theta_G \\ -\sin\alpha & \cos\alpha & 0 \\ -\cos\Theta_G\cos\alpha & -\cos\Theta_G\sin\alpha & \sin\Theta_G \end{pmatrix} \begin{pmatrix} k_{dx} \\ k_{dy} \\ k_{dz} \end{pmatrix}.$$

Note that the y" component of the diffracted light wave vector $k_{dy}$" is given by Equation (10), where $k_{dy}$" is not zero when $\alpha$ is not zero.

$$k_{dy''} = -k_{dx}\sin\alpha + k_{dy}\cos\alpha \quad (10)$$

$$= -(k_{sx} + 2\pi mG)\sin\alpha + k_{sy}\cos\alpha$$

$$= -2\pi mG\sin\alpha$$

This means when the grating pattern is tilted, the diffracted light rainbow does not go toward the probe axis direction. In other words, at least part of the SEE light does not reach the center of the field of view due to a lateral shift.

Here, we define an angle of illumination rainbow lateral shift, $\theta_{RLS}$, as Equation (11).

$$\theta_{RLS} = \arctan\frac{k_{dy''}}{k_{dz''}}\bigg|_{k_{dx''}=0} \quad (11)$$

Now, we introduce $\lambda_0$, which is the wavelength satisfying the grating equation when $\alpha=0$ and $k_{dx''}=0$, $$n_s|_{\lambda=\lambda_0}\sin\theta_i + \sin\left(\frac{\pi}{2}-\Theta_G\right) = -mG\lambda_0. \quad (12)$$

When $\alpha$ is small and $k_{dy''} \ll k_d$, $\theta_{RLS}$ can be approximated as $$\theta_{RLS} \cong \frac{k_{dy''}}{k_d}\bigg|_{k_{dx''}=0} = (-mG\lambda|_{k_{dx''}=0})\cdot\alpha \quad (13)$$
$$\cong -mG\lambda_0\alpha$$

which means the rainbow lateral shift angle $\theta_{RLS}$ is proportional to the grating pattern inclination angle $\alpha$.

Simulation Results

Table 1 shows parameters based on an exemplary design of a prototype color SEE probe fabricated by the applicant of the present application. Here, a simulation was performed to check rainbow curve shift of blue channel light with respect to the center of the field of view on the illumination plane.

TABLE 1

Sample Probe parameters

| Probe parameter | Value |
|---|---|
| Mirror surface angle (deg) $\Theta_M$ | 41.4 |
| Grating surface angle (deg) $\Theta_G$ | 42.7 |
| Grating groove density (lines/mm) G | 1000/1.54 = 649.4 |
| Spacer material | OHARA S-BSL7 |
| Diffraction order for blue channel m | −6 |
| Wavelength at FOV center when $\alpha = 0$ (nm) $\lambda_0$ | 416.4 |

For refractive index of S-BSL7, we use the Sellmeier equation $$n_s^2 = 1 + \frac{B_1\lambda^2}{\lambda^2-C_1} + \frac{B_2\lambda^2}{\lambda^2-C_2} + \frac{B_3\lambda^2}{\lambda^2-C_3} \quad (14)$$

with the coefficients of the Sellmeier equation shown in Table 2, where each term of the sum represents an absorption resonance of strength $B_i$ at a wavelength $\sqrt{C_i}$.

TABLE 2

Sellmeier coefficients of S-BSL7

| Coefficient | Value |
|---|---|
| $B_1$ | 1.1515019 |
| $B_2$ | 0.118583612 |
| $B_3$ | 1.26301359 |
| $C_1$ | 0.010598413 (μm²) |
| $C_2$ | −0.011822519 (μm²) |
| $C_3$ | 129.617662 (μm²) |

Figure 8A:
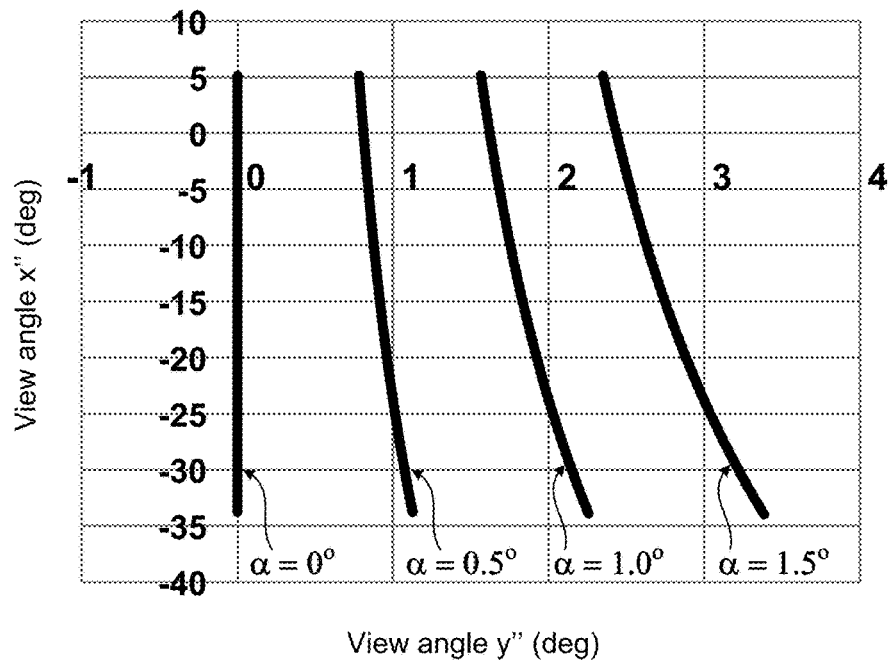
FIG. 8A shows the view angles of the spectrally dispersed illumination line (rainbow curve).

Now, FIG. 8A shows the view angle of the rainbow curve calculated by Eq. (9). The wavelength range is 400 to 480 nm. The grating pattern tilt $\alpha$ is 0, 0.5, 1.0, and 1.5 degrees. The view angle is measured from the probe axis (z"). The view angle is calculated as arctangent of $$\frac{k_{dy''}}{k_{dz''}}, \text{ and } \frac{k_{dx''}}{k_{dz''}}$$

for the y" and x" directions, respectively. Note that x" is the spectrally encoding direction.

Figure 8B:
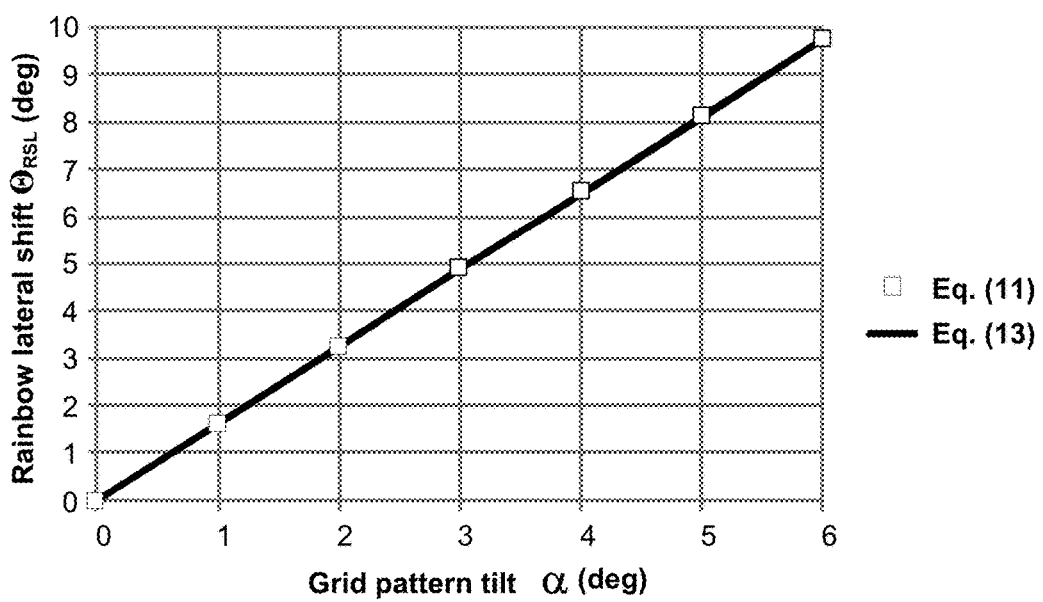
FIG. 8B shows the angle of rainbow lateral shift $\theta_{RLS}$ as a function of grating pattern tilt α.

FIG. 8B shows the angle of rainbow lateral shift $\theta_{RLS}$ for grating pattern tilt $\alpha$ calculated by Eq. (11), and its approximation calculated by Eq. (13). In this range of wavelengths and angles, the results plotted in FIG. 8B show Eq. (13) is a good approximation to values calculated by Eq. (ii). Here $-mG\lambda_0$ is 1.62. The results show that when the grating pattern is tilted by 1 degree but the other probe/sheath parts are assembled as designed in the example described above, there will be a blind area (obscuration area) of 3.2 degrees in diameter at FOV center even if we correct the imaging data in post processing.

The results shown in FIGS. 8A and 8B indicate that there can be a blind area at the FOV center when the grating pattern is tilted. The same type of error would be expected with any other misalignment, as described above. To avoid this obscuration, one option could be to increase the precision of assembly to make the tolerance for the tilt as close to zero as possible. However, this solution will increase the fabrication time and costs. Another option is to compensate this tilt effect by changing other parts assembly angles.

One option can be to attach the fiber/GRIN lens assembly on the spacer in such a way that $k_{dy''}=0$ when $k_{dx''}=0$. Instead of Eq. (3), change ray angle from GRIN lens to the grating surface to satisfy $$k_{dy''}|_{k_{dx''}=0} = \{-(k_{sx}+2\pi mG)\sin\alpha + k_{sy}\cos\alpha\}|_{k_{dx''}=0} = 0. \quad (15)$$

Another option is to tilt the probe optical axis from drive cable rotation axis by an angle of the rainbow lateral shift $\theta_{RLS}$. Therefore, in the fabrication step, it would be advantageous to actively perform an alignment process where, for example, a laser beam can be introduced into the probe to aide in the alignment of the distal optics so as to ensure that the rainbow light from the probe can go through rotation axis direction. In both cases it is important to minimize grating pattern tilt because tilting parts by a large angle is not easy if the size of the endoscope is limited.

Therefore, in order to know the effects of active alignment, the applicant has developed a simulation model for tilted grating pattern in forward view SEE imaging. The simulation results for an exemplary SEE color probe confirm that if the pattern is tilted and other parts are assembled as conventionally designed a blind area at the FOV center exists. Therefore, an alignment solution presented herein can avoid or at least minimize the obscuration of the center FOV, and therefore improved imaging results can be attained. Notably, the simulation model can be used to estimate a priori the amount of inclination (an alignment range) to ensure that no obscuration occurs at the center of the illumination FOV.

<SEE Probe Method of Alignment>

Figure 9A:
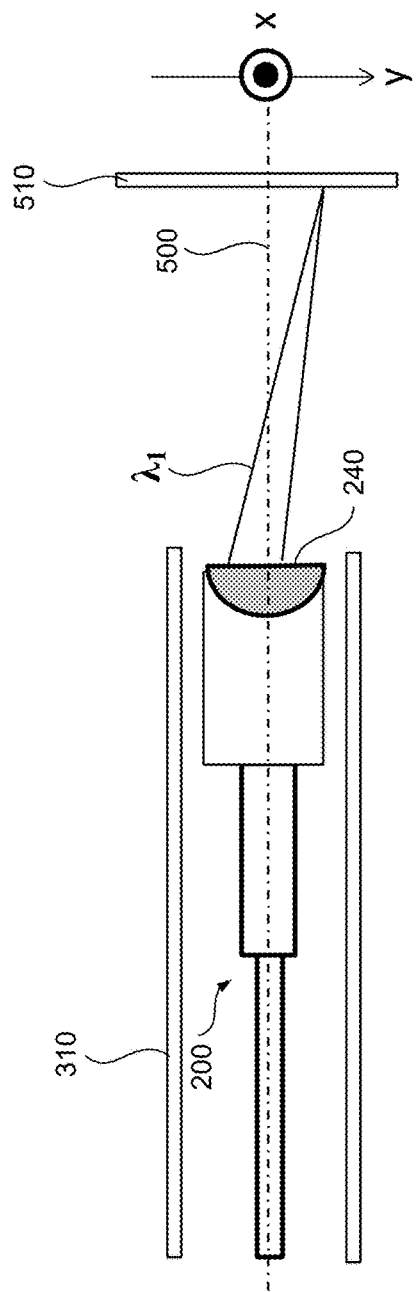
FIGS. 9A and 9B illustrate an example of a method of active alignment performed during the probe fabrication process of fixing the distal optics of probe 200 to a drive cable 310.
Figure 9B:
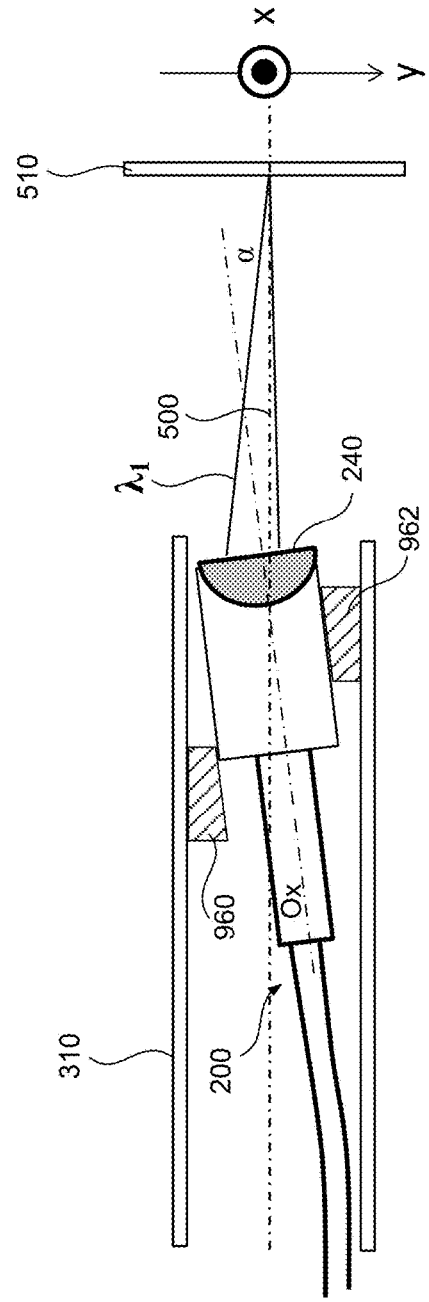
Figure 10B:
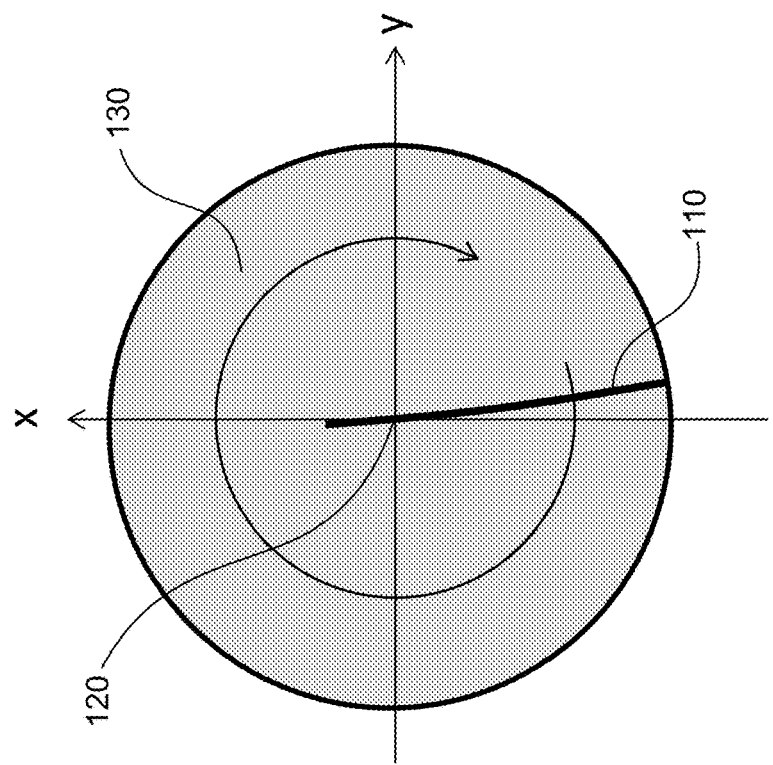
FIGS. 10A and 10B show the field of view observed at the imaging plane during an active alignment process using a broadband dispersed light line.
Figure 10A:
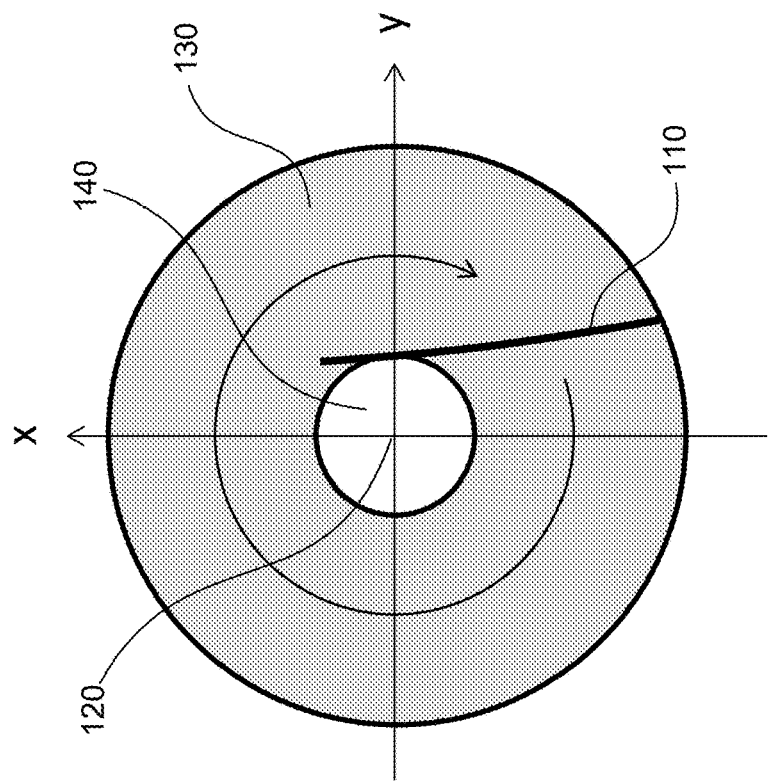

FIGS. 9A and 9B show an example of an active alignment performed during the probe fabrication process of fixing the distal optics of probe 200 to the drive cable 310. FIGS. 10A and 10B show the field of view observed at the imaging plane during the active alignment process.

An example of the active alignment can be performed as shown in FIGS. 9A and 9B. FIG. 9A shows the illumination optics assembly of the probe 200 and the drive cable 310 viewed from the x direction in the x, y, z coordinate system. In this example, the illumination optics of probe 200 and drive cable 310 are aligned such that the drive cable axis 500 is parallel to (an concentric with) the axis Ox of the optical probe. In this case, due to the fabrication errors described above, spectrally encoded illumination line 510 does not pass the axis Ox of the illumination optics of probe 200. As a result, the illumination light at the field of view does not pass the drive cable axis 500, and thus it does not irradiate the area 140 around the center 120 of the scanned area 130, as shown in FIG. 10A.

To ensure that the illumination light irradiates the center 120 of the scanning area 130, in the fabrication step of fixing the illumination optics of probe 200 and drive cable 310, an active alignment is performed. In the active alignment, a beam of light (e.g., laser beam) can be transmitted through the probe 200 and a screen or a sensor located in front of the distal end of probe 200, for example, at the working distance (Wd), can be used to actively check where the drive cable axis 500 is located on the screen or sensor. Then by introducing light from a broadband light source like a supercontinuum laser, LED, or lamp into the fiber 202 of the illumination optics, it is possible to monitor directly or indirectly when the illumination line no passes the axis 500. When fixing the illumination optics of probe 200 with the drive cable 310, we can tilt the illumination optics of probe 200 as shown in FIG. 9B so that the spectrally encoded illumination line no passes the drive cable axis 500 and the illumination light arrives to the center of the field of view, as shown in FIG. 10B. Once the alignment process ensures that the spectrally encoded illumination line no passes the drive cable axis 500 and the illumination light arrives to the center of the field of view, it is possible to secure (fix) the optics of the probe 200 to the drive cable 310, for example, by mechanical retaining elements 960 and 962, as shown in FIG. 9B. Mechanical retaining elements 960 and 962 used for aligning and securing (fixing) the optics of the probe 200 to the drive cable 310 can be prefabricated tubular structures or can be deposits of epoxy or resin that serve to hold one or more optical elements of the probe 200 at the desired angle.

In this manner, SEE optical probe 200 can be arranged such that the probe axis Ox is at an inclination angle α with respect to the axis 500 of the drive cable 310. The inclination angle can be obtained from the above-described inclination calculation and simulation. That is, a range of inclination angles and corresponding rainbow lateral shift angles, as those shown in FIGS. 8A and 8B, can be used to align the distal optics of the SEE probe in a manner to ensure that the illumination light arrives to the center of the field of view and obscuration is avoided.

Figure 11A:
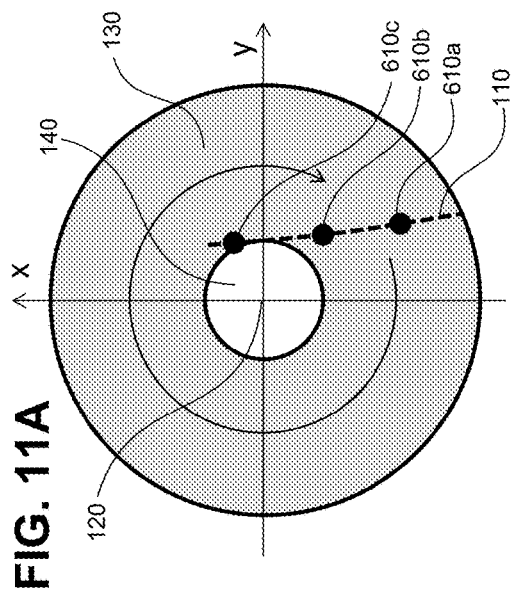
FIGS. 11A and 11B show the field of view observed at the imaging plane during an active alignment process using broadband dispersed light spots.
Figure 11B:
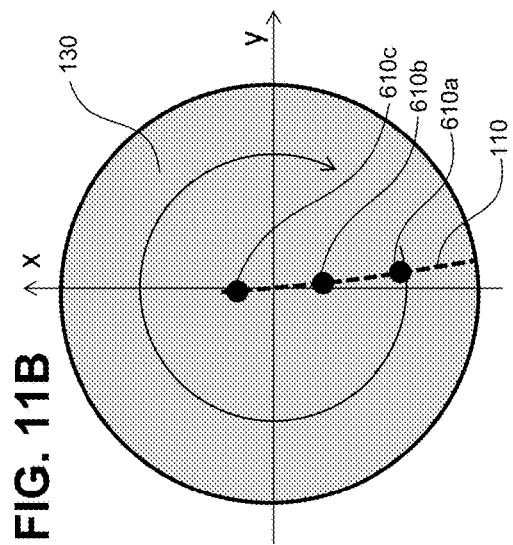

In the alignment above, multiple monochromatic light sources which have different wavelengths can be used instead of using broadband light source. In this case, multiple light spots 610 (610a, 610b, 610c) which is light of a specific wavelength diffracted by the grating 240 appear on the screen or sensor as shown in FIG. 11A. From the spots 610, it is possible to estimate the location of spectrally encoded illumination line no which is diffracted light from the illumination optics of probe 200. Therefore, to ensure that no obscuration area remains in the field of view, as shown in FIG. 11B, we can tilt the illumination optics of probe 200 within the drive cable 310, as shown in FIG. 10B, until the spectrally encoded illumination line no passes the drive cable axis 500.

When the probe generates diffracted light in multiple orders, one monochromatic light source can be used in the alignment above. For example, the probe in FIG. 5A could generate blue light in −6th order, but at the same time there is light diffracted in other orders, for example, in −5th order and −4th order (shown as lambda1-3, respectively).

Figure 12A:
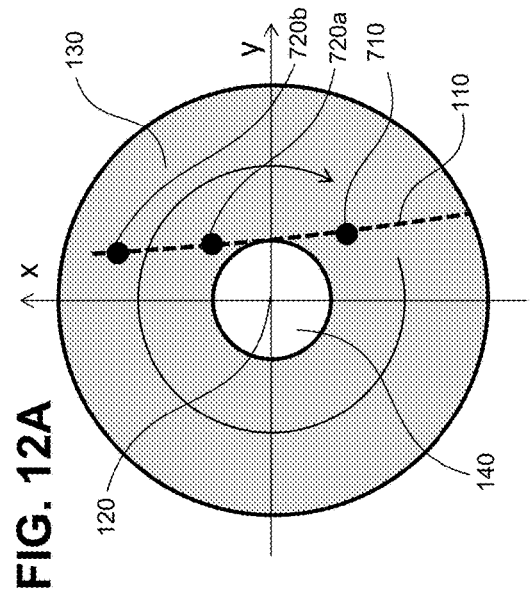
FIGS. 12A and 12B show the field of view observed at the imaging plane during an active alignment process using a single color dispersed light spots.
Figure 12B:
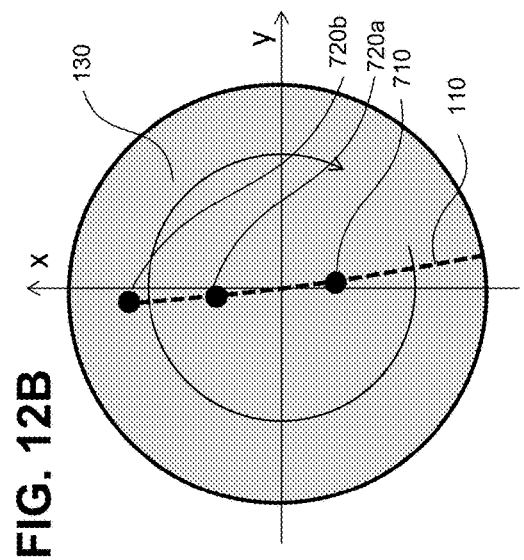

In this case of having diffracted light in multiple orders, one light spot 710 and two light spots 720 (720a, 720b) which are light diffracted in −6th order and −5th/−4th orders by the grating 240, respectively, appear on the screen or sensor as shown in FIG. 12A. From the spots 710 and 720, it is possible to accurately estimate the location of spectrally encoded illumination line no which is diffracted light from the illumination optics of probe 200 when broadband light is input into the probe. Here too, we can tilt the illumination optics of probe 200 as shown in FIG. 10B so that spectrally encoded illumination line no passes the drive cable axis 500 and the entire field of view is accurately illuminated as shown in FIG. 12B.

As discussed above, in the technical simulation, the spectrally encoded illumination line 110 on the target sample can be a slightly curved. Any negative effects cause by this curve on the image can be safely and accurately compensated in post processing. For example, by SEE imaging using calibration chart which can have fixed pattern like grid, we can figure out a relation between wavelength-time coordinates (data from spectrometer) and polar coordinates or Cartesian coordinates (processed image) for the curved illumination line. By applying the relation into post processing we can compensate data in wavelength-time domain from the spectrometer sensor into a corrected image.

<Imaging System>

Figure 13:
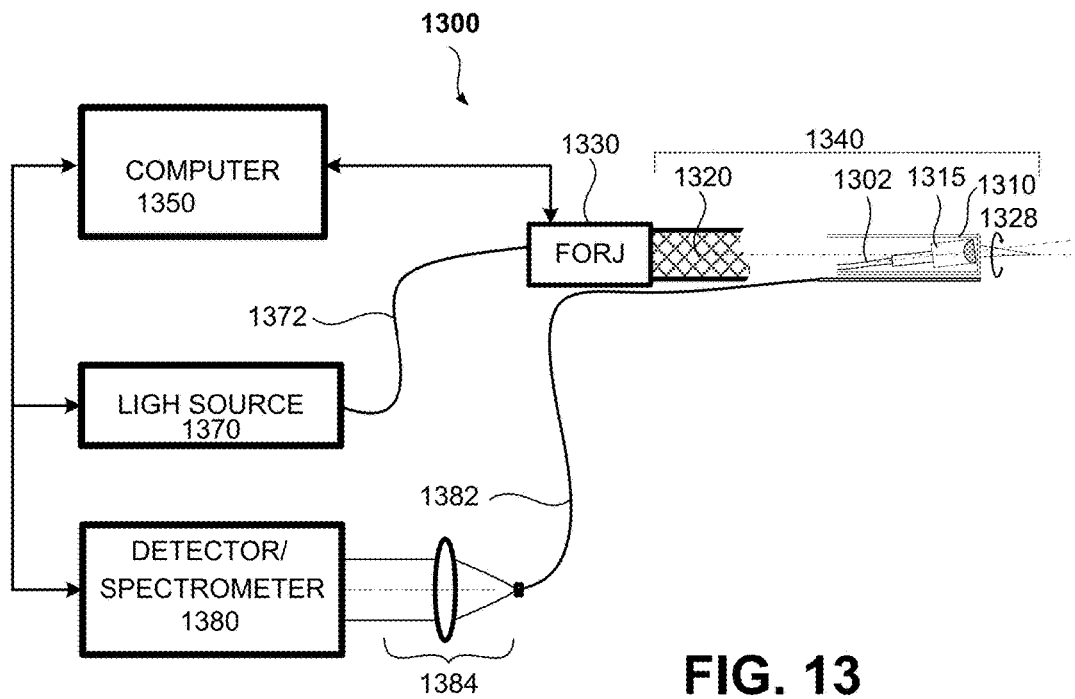
FIG. 13 is a diagram of an imaging system including the SEE endoscope according to an exemplary embodiment of the present disclosure.

A system 1300 to acquire an image using the SEE probe according to an exemplary embodiment of the present disclosure is shown in the diagram of FIG. 13. The system 1300 of FIG. 13 includes, for example, a light source 1370, a detector/spectrometer 1380, a fiber optic rotary joint (FORJ) 1330, an imaging wand 1340, and an image processing computer 1350. The light source 1370 can be a supercontinuum laser or lamp that outputs light of broadband spectrum, or laser diode or an LED that outputs light of a single color or a narrow band spectrum, or a source of other electro-magnetic radiation. The range of the wavelength can be within the visible region, which is from about 400 nm thorough 800 nm. However, other wavelengths may also be used. In the exemplary imaging system 1300, the light can be directly guided or otherwise coupled into a source fiber, which may be referred to as an illumination fiber 1372. The illumination fiber 1372 can be connected to the FORJ 1330, and the light further guided to (and/or associated with) the illumination fiber 1302 of the imaging wand or SEE probe 1340.

The SEE probe 1340 is connected at the proximal end thereof to the FORJ 1330. The SEE probe 1340 includes the illumination fiber 1302 and an assembly of distal optics 1315 arranged within a drive cable 1310; and the drive cable 1310 in turn is arranged within an outer sheath 1320. In this manner, illumination light emitted from light source 1370 is delivered to the distal optics assembly 1315, and then diffracted by a grating onto a forward-viewing imaging plane. The light scattered back from an object or target sample (e.g., tissue) can be collected by detecting fibers arranged around the distal end of the SEE probe 1340, and the collected light is guided by one or more detection fibers 1382, which are arranged outside the FORJ 1330. The detection fiber 1382 can be connected to the detector/spectrometer 1380 via a collimating or dispersing optical system 1384. The detector/spectrometer 1380 can detect the intensity of a selected wavelength. This exemplary function of detecting the selected wavelength can be performed by the spectrometer.

By mechanically rotating the wand or probe 1340 in a direction 1328 with a mechanical scanning unit contained within the FORJ 1330, it is possible to obtain a two-dimensional image of the target sample. The mechanical scanning unit (not shown) can be implemented by, e.g., a Galvo scanner or motor to rotate the drive cable 310 together with the illumination fiber 1302 and the distal optics assembly 1315. Computer 1350 includes one or more microprocessors configured to control and operate the various parts of system 1300, by executing computer-executable instructions (program code). Computer 1350 can also be programmed to reconstruct images based on signals obtained from detector/spectrometer 1380.

Figure 14:
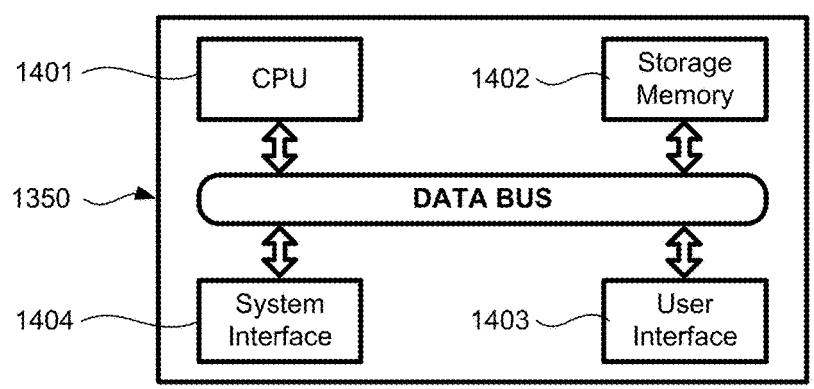
FIG. 14 is a block diagram of an exemplary imaging console.

FIG. 14 a schematic block diagram of a control and processing system applicable to the system illustrated in FIG. 13. As shown in FIG. 14, the computer control system is representative of computer 1350 shown in FIG. 13. In FIG. 14, the computer 1350 includes central processing unit (CPU) 1401, a storage memory (RAM) 1402, a user input/output (I/O) interface 1403, and a system interface 1404. The computer 1350 illustrated in FIG. 14 can issue a command that can be transmitted to the imaging system 1300 via the system interface 1404. A touch panel screen can be included as part of the user interface unit/imaging processor, in addition a key board, mouse, joy-stick, ball controller, and foot pedal can also be included as part of the user interface. The user can cause a command to be initiated to observe inside a lumen of the human body through the exemplary front-view SEE probe using the user interface unit/imaging processor. For example, when the user inputs a command via the user interface 1403, the command is transmitted to the central processing unit CPU 1401 for execution thereby causing the CPU to issue a command via the system interface 1404 to one or more of the light source 1370, the detector/spectrometer 1380, or the FORJ 1330.

The CPU 1401 is comprised of one or more processors (microprocessors) configured to read and perform computer-executable instructions stored in the storage memory 1402. The computer-executable instructions may include program code for the performance of the novel processes, methods and/or calculations disclosed herein.

The computer 1350 functions as imaging processor that can be programmed to apply exemplary image processing such as noise reduction, coordinate distortion correction, contrast enhancement and so on. After or even during the image processing is performed, the data can be transmitted from the imaging processor to a display (not shown). A liquid crystal display (LCD) can be the display. The display can display, for example, the individual images obtained from a single color or a composite color image according to the various exemplary embodiments of the present disclosure. The display can also display other information than the image, such as the date of observation, what part of the human body is observed, the patient's name, operator's name and so on.

The CPU 1401 is configured to read and perform computer-executable instructions stored in the Storage/RAM 1402. The computer-executable instructions may include those for the performance of the methods and/or calculations described herein. For example, CPU 1401 may calculate the angular momentum or speed of rotation of the SEE probe, and can use that information (rotation speed or angular momentum) to operate the FORJ. In this manner, computer 1350 can obtain a new set of images where their angular positions are corrected. Storage/RAM 1402 includes one or more computer readable and/or writable media, and may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage/RAM 1402 may store computer-readable data and/or computer-executable instructions. The components of the processor may communicate via a bus.

The system I/O interface 1404 provides communication interfaces to input and output devices, which may include a keyboard, a display, a mouse, a printing device, a touch screen, a light pen, an optical storage device, a scanner, a microphone, a camera, a drive, communication cable and a network (either wired or wireless).

The system I/O interface 1404 also provides communication interfaces to input and output devices. The detector may include, for example a photomultiplier tube (PMT), a photodiode, an avalanche photodiode detector (APD), a charge-coupled device (CCD), multi-pixel photon counters (MPPC), or other. Also, the function of detector may be realized by computer executable instructions (e.g., one or more programs) recorded on a Storage/RAM 1402.

In an exemplary operation, the user can place the exemplary SEE probe into a sheath, and then can insert such arrangement/configuration into a predetermined position of a human body. The sheath alone may be inserted into the human body in advance, and it is possible to insert the SEE probe into the sheath after sheath insertion. The exemplary probe can be used to observe inside human body and works as an endoscope such as arthroscopy, bronchoscope, sinuscope, vascular endoscope and so on.

<Definitions>

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The term "substantially", as used herein means that, within fabrication parameters and/or measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

The foregoing merely illustrates the principles of the disclosure. Various modifications and alterations to the described exemplary embodiments will be apparent to those skilled in the art in view of the teachings herein. Indeed, the arrangements, systems and methods according to the exemplary embodiments of the present disclosure can be used with any SEE system or other imaging systems, and for example with those described in U.S. Pat. Nos. 6,341,036; 7,796,270; 7,843,572; 7,859,679; 8,045,177; 8,145,018; 8,780,176; and 8,812,087; and U.S. Patent Application Nos. 2008/0013960 and 2011/0237892; and PCT publications WO2015/116951 and WO2015116939, the disclosures of which are incorporated by reference herein in their entireties.

In describing example embodiments illustrated in the drawings, specific terminology is employed for the sake of clarity. However, the disclosure of this patent application is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A probe having a proximal end and a distal end arranged along a longitudinal axis of a drive cable, the probe comprising:
    a light guiding component;
    a light focusing component; and
    a grating component,
    wherein the probe is configured for guiding light from the light guiding component, through the light focusing component, and to the grating component, and then forwarding a spectrally dispersed light line from the grating component towards an image plane,
    wherein a distal optics assembly comprising the light guiding component, the light focusing component, and the grating component are arranged inside the drive cable such that at least one wavelength of the spectrally dispersed light line goes towards the longitudinal axis of the drive cable,
    wherein the grating component includes a grating pattern configured to forward the spectrally dispersed light line onto the image plane,
    wherein the spectrally dispersed light line is projected onto the image plane at a lateral shift angle with respect to a center of the image plane, and
    wherein the distal optics assembly is arranged at an angle with respect to the longitudinal axis of the drive cable, so as to minimize the lateral shift angle.

2. The probe according to claim 1, wherein the grating component comprises a triangular grating.

3. The probe according to claim 1, wherein the probe is a spectrally encoding endoscopy (SEE) probe.

4. The probe according to claim 1, wherein the grating component is transmissive grating configured to spectrally disperse monochromatic light to form the spectrally dispersed light line with two or more of transmitted orders of diffracted monochromatic light.

5. The probe according to claim 4, wherein the grating component is configured to form the spectrally dispersed light line with the $4^{th}$, $5^{th}$, and $6^{th}$ orders of diffracted monochromatic light.

6. The probe according to claim 1, wherein the light focusing component is a gradient index (GRIN) lens or a ball lens.

7. The probe according to claim 1, wherein one or more elements of the distal optics assembly is arranged at the angle with respect to the longitudinal axis of the drive cable, such that the at least one wavelength of the spectrally dispersed light line goes towards the longitudinal axis of the drive cable.

8. The probe according to claim 1, wherein the light focusing component and the grating component are arranged inside the drive cable at the angle with respect to the longitudinal axis of the drive cable, such that the at least one wavelength of the spectrally dispersed light line goes towards the longitudinal axis of the drive cable.

9. A method of aligning distal end optics of an endoscopic probe, the method comprising:
    arranging a distal optics assembly comprising a light guiding component, a light focusing component, and a grating component along a longitudinal axis of a drive cable; and
    guiding light from the light guiding component, through the light focusing component, and to the grating component, and then forwarding a spectrally dispersed light line from the grating component towards an image plane,
    wherein arranging the grating component inside the drive cable includes arranging one or more of the light guiding component, the light focusing component, and the grating component at an angle with respect to the longitudinal axis of the drive cable such that at least one wavelength of the spectrally dispersed light line goes towards the longitudinal axis of the drive cable,
    wherein the grating component includes a grating pattern configured to forward the spectrally dispersed light line onto the image plane, wherein the spectrally dispersed light line is projected onto the image plane at a lateral shift angle with respect to a center of the image plane, and wherein the one or more of the light guiding component, the light focusing component, and the grating component is arranged at the angle with respect to the longitudinal axis of the drive cable, so as to minimize the lateral shift angle.

10. The method according to claim 9, further comprising:

analyzing a real-time image of the spectrally dispersed light line using an image sensor or a screen to confirm correct alignment of the distal end optics, by determining whether the at least one wavelength of the spectrally dispersed light line goes towards the longitudinal axis of the drive cable.

11. The method according to claim 9, further comprising:

adjusting a position of the projected spectrally dispersed light line on the mage plane such that the least one wavelength of the spectrally dispersed light line goes to the center of the image plane.

* * * * *